United States Patent [19]
Rozmus et al.

[11] Patent Number: 6,069,967
[45] Date of Patent: May 30, 2000

[54] METHOD AND APPARATUS FOR ILLUMINATING AND IMAGING EYES THROUGH EYEGLASSES

[75] Inventors: J. Michael Rozmus, Medford, N.J.; Marcos Salganicoff, Philadelphia, Pa.

[73] Assignee: Sensar, Inc., Moorsetown, N.J.

[21] Appl. No.: 08/964,359

[22] Filed: Nov. 4, 1997

[51] Int. Cl.[7] .................. G06K 9/00; A61B 3/14
[52] U.S. Cl. .................. 382/117; 348/78; 351/206; 351/219
[58] Field of Search .......... 382/115–118; 340/439, 340/575, 576; 348/77, 78, 131, 132, 306, 308; 351/200, 205, 208–211, 213, 219, 221, 206, 207

[56] References Cited

U.S. PATENT DOCUMENTS

| | | | |
|---|---|---|---|
| 4,109,237 | 8/1978 | Hill | 382/117 |
| 4,620,318 | 10/1986 | Hill | 382/2 |
| 4,641,349 | 2/1987 | Flom et al. | 382/2 |
| 4,687,344 | 8/1987 | Lillquist | 348/164 |
| 5,010,412 | 4/1991 | Garriss | 348/371 |
| 5,016,282 | 5/1991 | Tomono et al. | 382/2 |
| 5,270,924 | 12/1993 | Hideshima | 382/117 |
| 5,291,560 | 3/1994 | Daugman | 382/2 |
| 5,359,669 | 10/1994 | Shanley et al. | 382/117 |
| 5,614,967 | 3/1997 | Ishikawa et al. | 351/209 |
| 5,801,763 | 9/1998 | Suzuki | 348/77 |

*Primary Examiner*—Bhavesh Mehta
*Attorney, Agent, or Firm*—Buchanan Ingersoll, P.C.

[57] ABSTRACT

A reliable method of illuminating and imaging an eye through eyeglasses uses a monochromatic light source with the smallest possible source area, a camera with an imager that exhibits minimal blooming, and a narrow-bandwidth optical bandpass filter to filter out most of the ambient illumination while passing most of the light from the system's own illuminator. In an alternative embodiment, a partially-transparent mirror is used to make the light source appear to be on the optical axis of the camera as viewed from the subject's eye.

18 Claims, 1 Drawing Sheet

METHOD AND APPARATUS FOR ILLUMINATING AND IMAGING EYES THROUGH EYEGLASSES

FIELD OF THE INVENTION

The invention relates to identifying individuals from facial images, and more particularly from images of the eye.

BACKGROUND OF THE INVENTION

There are several methods known as biometrics for recognizing or identifying an individual from personal biological characteristics. Some of these methods involve imaging of the face or eye and analyzing the facial features, retinal vascular patterns of the eye, or patterns in the iris of the eye. In recent years there has been a demand for more reliable systems to identify individuals, particularly those persons who desire access to a secured area or system. A common example of such a secured system are automated teller machines which allow authorized users to conduct banking transactions. Many of these systems are used by a wide variety of people. Very often these people demand quick as well as accurate identification.

A technique for accurately identifying individuals using iris recognition is described in U.S. Pat. No. 4,641,349 to Flom et al. and in U.S. Pat. No. 5,291,560 to Daugman. The systems described in these references require clear, well-focused images of the eye. The presence of eyeglasses tends to interfere with good eye images because of reflections on the eyeglasses. Contact lenses may also cause reflections that interfere with eye imaging. However, because contact lenses have a greater curvature than eyeglasses reflections from contact lenses are smaller and less of a problems than reflections from eyeglasses.

Reflections may come from the system's own illumination. In this case, calculations show that the irradiance (illuminance for visible light) at the camera lens from the specular reflection of an illuminator from eyeglasses is on the order of 1000 times greater than the irradiance at the camera of the image of the eye caused by diffuse reflection of the illuminator. A camera viewing the eye must have a combination of lens, aperture, and exposure time that will result in a sufficiently bright image of the eye. Thus, the much brighter specular reflection of the illuminator will saturate the picture elements (pixels) of the camera's image sensor that cover the area of the specular reflection, and all information about the portion of an eye image obscured by this reflection will be lost. Furthermore, the values of pixels surrounding the area of the specular reflection may be corrupted by the saturated pixels in a phenomenon called "blooming". This occurs because the pixels of charge-coupled devices (CCD's), the most common electronic imagers, are not well isolated from one another.

Reflections may also come from ambient illumination, such as bright sunlight. The irradiance generated by such reflections depends on specific ambient conditions, but the power of direct sunlight is comparable to or greater than the power of any safe artificial illuminator, therefore ambient illumination can sometimes cause the same kind of obscuring reflection as the system's own artificial illuminator.

It is possible to ask the subject to remove his or her eyeglasses in order to get a good image of the subject's eye. However, this is potentially annoying, and the subject may refuse to remove the glasses, or avoid using the system. Consequently, there is a need for an imaging system that can obtain useful images of the eye while minimizing the effect of specular reflections without requiring the subject to remove any eyeglasses or contact lenses that may be present.

SUMMARY OF THE INVENTION

We provide a reliable method and apparatus for illuminating and imaging an eye through eyeglasses or contact lenses. First we select a light source with the smallest possible source area. Second we use a camera with an imager that has high isolation between adjacent pixels and thus minimal blooming, in contrast to the commonly used standard CCD imager. Third we choose the light source to be monochromatic, or nearly monochromatic with a narrow spectral bandwidth, with a center wavelength in the range of 700 to 800 nanometers for balance of visibility, imager sensitivity, and iris absorption properties. Fourth we prefer to place a narrow-bandwidth optical bandpass filter on the optical axis of the camera. This filter has a center wavelength and bandwidth matching the light source of the illuminator to filter out most of the ambient illumination while passing most of the light from the system's own illuminator.

In an alternative embodiment, we use a partially-transparent mirror to make the light source appear to be on the optical axis of the camera as viewed from the subject's eye.

DESCRIPTION OF THE PREFERRED EMBODIMENTS

Figure 1:
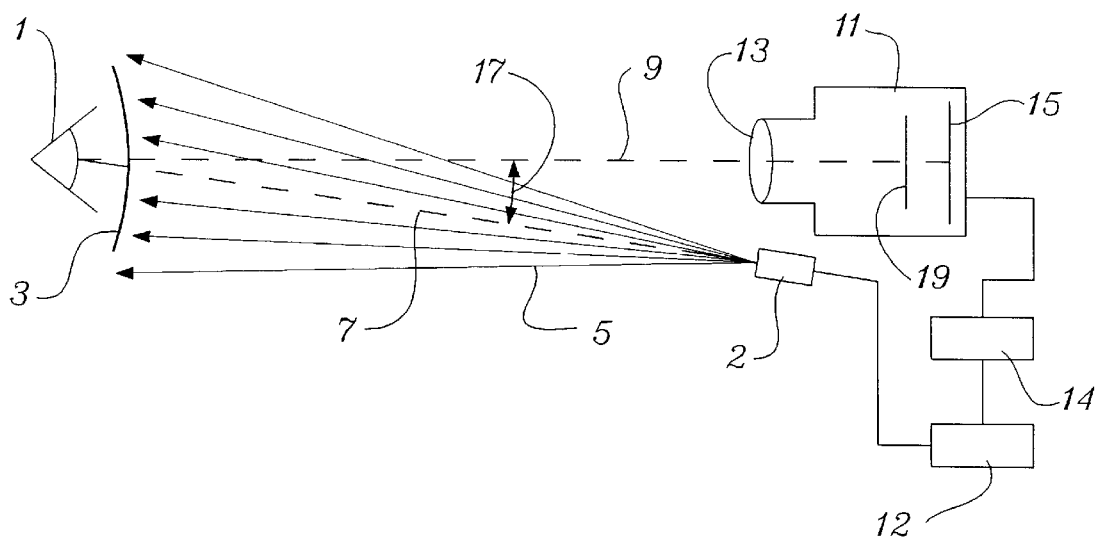
FIG. 1 is a diagram showing a first preferred embodiment of the present invention in which the light source of the illuminator is adjacent to the camera.

In FIG. 1, we show a diagram of a first preferred embodiment of the present invention. The eye 1 of a subject with eyeglass lens 3 is looking into a camera 11 along the camera's optical axis 9. The eye is illuminated by a light source 2 having a small source area which emits a cone-shaped beam 5 with centerline 7 that is at an angle 17 from the optical axis 9. The angle 17 is a relatively small acute angle, preferably less than 15°, so that the illumination will be relatively even across the front surface of the eye 1. The exact shape of the emission pattern of the light source 2 is not critical, so long as the source area is small and the illumination across the front surface of the eye is fairly even.

The source area of the light source 2 is chosen so that the virtual image of its specular reflection off of the eyeglass lens 3 will appear small from the viewpoint of the camera 11. Specifically, the source area must be smaller than twice the largest area obscured by a specular reflection that can be tolerated in the image of the eye 1 seen through the eyeglass lens 3. This is because the reflected virtual image of the light source 2 in the eyeglass lens 3 appears to be half of its actual size, when compared to the size of the eye 1, in the worst case of an eyeglass lens 3 with a flat surface. Since the surfaces of modern eyeglass lenses are generally curved outward from the eye as shown in the drawing of eyeglass lens 3, these surfaces act as convex mirrors, reducing the apparent size of the virtual image of the source even more.

The light source 2 may be implemented with a single high-power light-emitting diode, a laser diode fed through an optical fiber, a laser fitted with a diverging lens, an incandescent lamp, or any other source that produces sufficient power in the appropriate spectral band from a small source area.

The small source area of the light source 2 has a notable disadvantage that must be carefully controlled. When the eye 1 of the subject views the light source 2, essentially all of the light entering the pupil of the eye 1 is focused on a small area of the retina forming an image of the light source 2. This concentration of energy is potentially more hazardous than viewing a more diffuse source with a larger source area. This hazard can be controlled and safety assured by careful control of the duration and intensity of output from the light source 2. Instead of leaving the light source 2 on during the time that a subject is present, the light source 2 is pulsed or flashed in synchronization with the exposure times of the camera 11. This can be done using a strobing device 12 and a controller 14 connected to the strobing device 12 and the camera or imager 11. Both the intensity and duration of these pulses are controlled to get the correct exposure of the images of the eye 1. This allows the retinal exposure to be kept well below internationally accepted safety limits, while still providing sufficient illumination.

The virtual image of the light source 2 from the specular reflection off of the eyeglass lens 3 is so bright compared to the image of the eye behind the eyeglass lens 3 that the virtual image generally saturates some of the pixels of the imager 15 in the camera 11, completely obscuring a portion of the image of the eye 1. Furthermore, this saturation distorts the values of the pixels immediately surrounding the image of the specular reflection of the source 2 in a phenomenon called "blooming" when the imager 15 is a charge-coupled device (CCD), the most common type. Newer CMOS (complementary metal-oxide semiconductor) or CID (Charge-Injection Device) imagers have much more electrical isolation between adjacent pixels than the CCD's, minimizing blooming. Because of the minimal blooming we prefer to provide a CMOS imager 15, such as the VLSI Vision VV5850, instead of the more common CCD imager, in order to further mitigate the negative effects of the already small specular reflection of the light source 2. There may be other imagers with high resistance to blooming available or developed in the future that could be used in place of a standard CCD imager.

All of the methods and apparatus described above will work for any wavelength of illumination from the light source 2 for which the imager 15 has sufficient sensitivity. CMOS, CCD, and other silicon-based imagers have relatively high sensitivity in the range of about 500–800 nanometers with sensitivity dropping off to near zero at about 300 nanometers on the low end and about 1050 nanometers on the high end.

In order to minimize the effect of ambient illumination, it is desirable for the illumination from the light source 2 to have a narrow spectral bandwidth so that a narrow optical bandpass filter 19 may be used in the camera to allow the imager 15 to see illumination from the light source 2 while not being able to see light at any other wavelengths. For example, the light source 2 may be implemented with a laser having a center wavelength of 750 nanometers and a spectral bandwidth of less than 10 nanometers. This would enable the use of a thin-film interference bandpass filter 19 with the same center wavelength and a 10-nanometer bandwidth. In the preferred embodiment of FIG. 1, the filter 19 is placed between the lens 13 and the imager 15 of the camera 11 because the center wavelength of the filter 19 is somewhat dependent on the angle of incidence of the light to be filtered. With proper optical design, there will be a location between the lens 13 and the imager 15 where all of the light going to the imager 15 will pass through the filter 19 at near normal angle of incidence.

The sun is very likely the worst case of interfering ambient illumination. At 750 nanometers, the worst case solar spectral irradiance is about 100 milliWatts per square centimeter per micron of spectral band. Within the 10-nanometer bandwidth of the filter 19, only 1 milliWatt per square centimeter of the sun's irradiance will be detectable by the imager 15. This level is less than or equal to the level of irradiance that the light source 2 produces at the eye 1. Thus the controlled illumination from the light source 2 is not overwhelmed by illumination from the sun even in worst-case sunny conditions.

The preceding example of illumination at 750 nanometers is also a good choice of wavelength because human eyes cannot see wavelengths greater than about 700–750 nanometers. In order that the imaging of the eye 1 be unobtrusive to the subject, it is desirable that the subject not be able to see the illumination from the light source 2.

When the iris portion of the eye is used for identification, it is important to be able to separate the iris portion from the rest of the eye image. Images of the eye taken with wavelengths of about 840–920 nanometers show a relatively low contrast between the brightness of the iris and the brightness of the surrounding sclera (the white of the eye) making the outer boundary of the iris difficult to locate. Biomedical research shows that the function of incident light absorption by the iris versus wavelength has a sharp drop at about 750–800 nanometers. Therefore, use of a wavelength of illumination of 750 nanometers or below, as in the example above, will increase the absorption by the iris and make the iris appear darker, thus improving the contrast between the iris and the sclera.

In summary, we prefer for the present invention to use a monochromatic, or nearly monochromatic, illumination with center wavelength in the range of 700–800 nanometers to balance the considerations of visibility to the subject, sensitivity of the imager 15, and contrast along the iris/sclera boundary.

Figure 2:
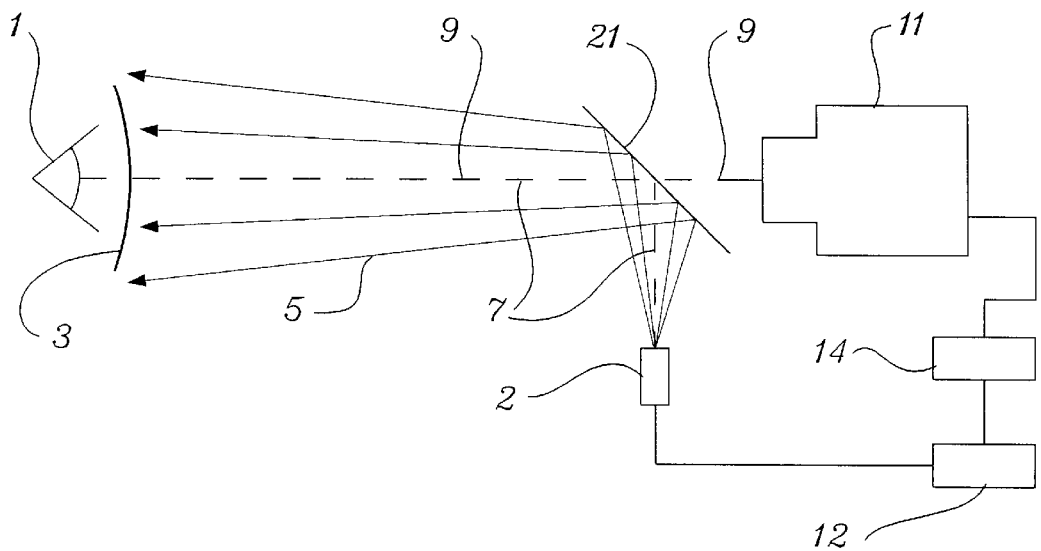
FIG. 2 is a diagram showing a second preferred embodiment of the present invention in which a partially-transparent mirror is used to make the light source of the illuminator appear to be directly on the optical axis of the camera.

In FIG. 2, we show a second preferred embodiment of the present invention. In this case a partially transparent mirror 21 is used to cause the centerline 7 of the cone-shaped light beam 5 from the light source 2 to coincide with the optical axis 9 of the camera 11 from the point of view of the eye 1 of the subject. This arrangement makes it easier to deliver even illumination across the front surface of the eye 1 at the cost of illumination losses through the partially-transparent mirror 21.

We have described the present invention as used for imaging the eye. However, there are other applications for this invention in which an image is taken of an object that is behind a lens or other light transmissive curved structure. For example, this method and apparatus could be used to obtain images of products packaged in light transmissive packaging. Such images could be used for quality control or product identification purposes.

The light transmissive structure is not limited to clear materials. That structure may allow passage of limited wavelenghts of light which could be visible or invisible to the human eye. A common example of such a structure are the plastics used in sunglasses.

Although we have shown certain present preferred embodiments of our invention, it should be distinctly understood that the invention is not limited thereto, but may be variously embodied within the scope of the following claims.

We claim:

1. An apparatus for obtaining an image of an object that is positioned behind a light-transmissive structure which structure has reflections from a light source that could obscure a portion of the object comprising:

a. an imager that exhibits minimal blooming positioned so that the object is within the imager's field of view; and b. a light source, having a source area smaller than twice a largest area obscured by a specular reflection that can be tolerated in the image of the object, positioned to direct a beam to the object along a first line that intersects a second line from the imager to the object at an acute angle.

2. The apparatus of claim 1 also comprising a bandpass filter in front of the imager.

3. The apparatus of claim 1 wherein the light source is monochromatic.

4. The apparatus of claim 3 wherein the light source emits light having a wavelength between 700 and 800 nanometers.

5. The apparatus of claim 1 wherein the imager that exhibits minimal blooming is a complementary metal-oxide semiconductor imaging device.

6. The apparatus of claim 1 also comprising a strobing device connected to the light source.

7. The apparatus of claim 6 wherein the imager has an exposure control and also comprising a controller connected to the exposure control and the strobing device for sychronizing the exposure control and the strobing device.

8. The apparatus of claim 1 wherein the light transmissive structure is eyeglasses.

9. The apparatus of claim 1 wherein the light source only emits light within a selected narrow spectral range and also comprising a bandpass filter in front of the imager, the bandpass filter allowing passage of light that is within the selected narrow spectral range and preventing passage of light that is outside of the selected narrow spectral range.

10. The apparatus of claim 1 also comprising a partially transparent mirror positioned to direct the beam from the light source along the optical axis of a camera system containing the imager.

11. A method for obtaining an image of a human eye comprising:

a. positioning an imager that exhibits minimal blooming such that the eye is in the imager's field of view;

b. directing a light beam from a light source, having a source area smaller than twice a largest area obscured by a specular reflection that can be tolerated in the image of the eye, to the eye along a first line that intersects a second line from the imager to the eye at an acuate angle; and c. recording an image of the eye using the imager.

12. The method of claim 11 wherein the light beam is monochromatic.

13. The method of claim 11 wherein the light beam has a wavelength between 700 and 800 nanometers.

14. The method of claim 11 wherein the imager that exhibits minimal blooming is a complementary metal-oxide semiconductor imaging device.

15. The method of claim 14 wherein the light beam is within a selected narrow spectral range and further comprising filtering light reflected from the eye to the imager in a manner to allow passage of only that light having wavelengths within the selected narrow spectral range.

16. The method of claim 11 also comprising strobing the light beam.

17. The method of claim 16 wherein the imager has an exposure control and also comprising synchronizing the exposure control and the strobing device.

18. The method of claim 11 also comprising filtering ambient illumination that is reflected from the eye along the optical axis.

\* \* \* \* \*